(12) United States Patent
Arpin et al.

(10) Patent No.: US 6,399,584 B1
(45) Date of Patent: Jun. 4, 2002

(54) PHARMACEUTICAL COMPOSITION CONTAINING EZRIN MUTATED ON TYROSINE 353

(75) Inventors: Monique Arpin, Paris (FR); Tiziana Crepaldi, Turin (IT); Alexis Gautreau, Paris; Daniel Louvard, Sceaux, both of (FR)

(73) Assignees: Institute Curie, Cedex (FR); Centre National de Recherche Scientfique, Paris (FR)

( * ) Notice: Subject to any disclaimer, the term of this patent is extended or adjusted under 35 U.S.C. 154(b) by 0 days.

(21) Appl. No.: 09/040,725

(22) Filed: Mar. 18, 1998

(51) Int. Cl.$^7$ ................................................ A61K 48/00
(52) U.S. Cl. ........................ 514/44; 536/23.1; 536/23.5; 435/69.1; 435/320.1; 435/455; 424/93.2
(58) Field of Search .............................. 536/23.1, 23.5; 530/350; 514/44; 435/320.1, 69.1, 455, 325; 424/93.2

(56) References Cited

PUBLICATIONS

Ngo et al., in The Protein Folding Problem and Tertiary Structure Prediction, 1994, Merz et al., (ed.), Birkhauser, Boston, MA, pp. 492–495, 1994.*
Anderson, Nature, vol. 392, 25–30, Apr. 1998.*
Gunzburg et al., vol. 1, No. 9, pp. 410–417, 1995.*
Mastrangelo et al., Seminars in Oncology, vol. 23, No. 1, pp. 4–21, 1996.*
Meng et al. (Gene Therapy of Cancer, Chapter I, pp. 3–20, 1999).*
Tait et al. (Clinical Cancer Res., vol. 5, 1707–1714, 1999).*
Algrain, M. et al. 1993. Ezrin contains cytoskeleton and membrane binding domains accounting for its proposed role as a membrane–cytoskeletal linker. *J. Cell Biol.* 120:129–139.
Arpin, M. et al. 1994. Membrane–actin microfilament connections: an increasing diversity of players related to band 4.1. *Current Opinion in Cell Biology* 6:136–141.
Bardelli, A. et al. 1992. Autophosphorylation promotes complex formation of recombinant hepatocyte growth factor receptor with cytoplasmic effectors containing SH2 domains. *Oncogene* 7:1973–1978.

Bretscher A. 1983. Purification of an 80,000–dalton protein that is a component of the isolated microvillus cytoskeleton, and its localization in nonmuscle cells. *J. Cell. Biol.* 97, 425–432.
Chen, C., and H. Okayama. 1987. High–efficiency transformation of mammalian cells by plasmid DNA. *Mol. Cell. Biol.* 7:2745–2752.
Crepaldi, T. et al. 1997. Ezrin is an effector of hepatocyte growth factor–mediated migration and morphogenesis in epithelial cells. *The Journal of Cell Biology* 138(2):423–434.
Derossi, D. et al. 1994. The third helix of the Antennapedia homeodomain translocates through biological membranes. *J. Biol. Chem.* 269:10444–10450.
Kreig, J. and T. Hunter. 1992. Indentification of the two major epidermal growth factor–induced tyrosine phosphorylation sites in the microvillar core protein ezrin, *J. Biol. Chem.* 267:19258–65.
Kreis, T. E. 1986. Microinjected antibodies against the cytoplasmic domain of vesicular stomatitis virus glycoprotein block its transport to the cell surface. *EMBO J.* 5:931–941.
Naldini, L. et al.. 1991. Scatter factor and hepatocyte growth factor are indistinguishable ligands for the MET receptor. *EMBO J.* 10:2867–2878.
Naldini, L. et al. 1995. Biological activation of pro–HGF (hepatocyte growth factor) by urokinase is controlled by a stoichiometric reaction. *J. Biol. Chem.* 270:603–611.
Tsukita, T. et al. 1997. ERM (ezrin/radixin/moesin) family: from cytoskeleton to signal transduction. *Current Opinion in Cell Biology* 9:70–75.
Vaheri, A. et al. 1997. The ezrin protein family: membrane–cytoskeleton interactions and disease associations. *Current Opinion in Cell Biology* 9:659–666.

* cited by examiner

*Primary Examiner*—Dave T. Nguyen
(74) *Attorney, Agent, or Firm*—Darby & Darby

(57) ABSTRACT

The invention relates to a pharmaceutical composition containing an effective amount of ezrin mutated on tyrosine 353, or a functional fragment or derivative thereof, in association with a pharmaceutically acceptable carrier, for use preferably in the prevention and/or treatment of tumors.

16 Claims, 11 Drawing Sheets

Positions shown at right: I 19, R 39, K 59, E 79, K 99, E 119, E 139, Q 159, R 179, M 199, V 219, F 239, I 259, I 279, I 299

FIG. 1B (Figure 1B shows a protein sequence chart with residues numbered from R 319 to I 579, arranged in a grid. A Y residue is circled in the sequence.)

FIG. 2A

|      | P | E1 | E2 | F1 | F2 |
|------|---|----|----|----|----|
| 175 − |   |    |    |    |    |
| 83 −  |   | ▬  | ▬  | ▬  | ▬  |
| 62 −  |   |    |    |    |    |
| 47.5 −|   |    |    |    |    |

```
Biotin                                    P
  |                                       |
RQIKIWFFQNRRMKWKKLRLQDYEEKTK
─────────────────────── ───────────
    Antennapedia              Ezrin 348-358
cell-permeable peptide
```

0   Y   pY

━  p85

US 6,399,584 B1

PHARMACEUTICAL COMPOSITION CONTAINING EZRIN MUTATED ON TYROSINE 353

FIELD OF THE INVENTION

The present invention relates to a pharmaceutical composition containing ezrin mutated on tyrosine 353, for controlling cell survival and apoptosis and for use preferably in the prevention and/or treatment of tumors.

BACKGROUND OF THE INVENTION

Throughout this application, various publications, issued patents and published patent specifications are cited. The bibliographic citation for each reference may be found at the end of the specification, immediately preceding the claims or within this specification. The disclosures of these publications are hereby incorporated by reference into the present disclosure to more fully describe the state of the art to which this invention pertains.

Ezrin was characterized as a component of brush-border and placental microvilli in the early 1980s (Bretscher et al., 1983). The family now consists of four members in vertebrates, namely ezrin, radixin, moesin (ERM proteins) and merlin (moesin-ezrin-radixin-like protein: also named schwannomin).

The structure of all family members consists of an amino-terminal globular domain followed by an a-helical region and a carboxy-terminal domain. The family belongs to the band 4.1 superfamily on the basis of sequence homology of the amino-terminal domain with the erythrocyte membrane-cytoskeleton linker protein band 4.1.

Ezrin, radixin and moesin are thought to work as cross-linkers between plasma membranes and actin-based cytoskeletons (Arpin et al., 1994).

Phosphorylation may regulate the conformation of the proteins induced by several growth factors. ERM proteins could be regulated by phosphorylation of different protein domains, including Tyr145 located in the amino-terminal domain and Tyr353 in the α-helical domain. These two residues are phosphorylated by EGF receptor (Krieg et al., 1992). Phosphorylation of the carboxy-terminal domain may also regulate the actin-binding ability of ERM proteins (Vaheri et al., 1997, Tsukita et al., 1997).

DISCLOSURE OF THE INVENTION

The authors of the present invention have recently shown that ezrin is an effector of hepatocyte growth factor-mediated migration and morphogenesis in epithelial cells (Crepaldi et al., 1997).

The authors of the present invention have now discovered that ezrin mutated on tyrosine 353 as shown in FIG. 1 impairs the ability of cells to survive in a collagen matrix, more particularly in a collagen type I matrix, and induces apoptosis, that is to say cell death. Such apoptosis could be due to a disruption of the signal transmission mediated by molecules of adhesion. In vivo, normal cells lie on a basal membrane which does not contain collagen type I. Tumor cells, and more particularly metastatic cells, may contact the extracellular matrix which contains collagen type I and are thus sensitive to the effect of ezrin mutated on tyrosine 353. Consequently ezrin mutated on tyrosine 353 is a good candidate for the prevention and/or treatment of tumors. Furthermore, ezrin mutated on tyrosine 353 could be useful to prevent metastasis and/or to lead to the apoptosis of migrating tumor cells involved in metastasis. which is a phenomenon due to a disruption of cell adhesion.

A subject of the present invention is thus a pharmaceutical composition containing an effective amount of ezrin mutated on tyrosine 353, or a functional fragment or derivative thereof, in association with a pharmaceutically acceptable carrier.

A further subject of the present invention is a pharmaceutical composition containing an effective amount of naked DNA or RNA encoding ezrin mutated on tyrosine 353, or encoding functional fragments or derivatives thereof, in association with a pharmaceutically acceptable carrier.

A still further subject of the present invention is a pharmaceutical composition containing an effective amount of a vector comprising an insert of DNA or RNA encoding ezrin mutated on tyrosine 353, or encoding fragments or derivatives thereof.

The pharmaceutical compositions of the invention are more particularly useful for the prevention and/or treatment of tumors, namely for the prevention and/or treatment of metastasis.

BRIEF DESCRIPTION OF THE FIGURES

FIG. 1 represents the amino acid sequence of human ezrin before the maturation by deletion of the first amino acid Met(SEQ ID No: 1).

The level of ezrin in cells overexpressing wild type ezrin (E) and ezrin mutant (F) was compared to the level of endogenous ezrin in cells transfected with the vector alone (P).

Figure 2C:
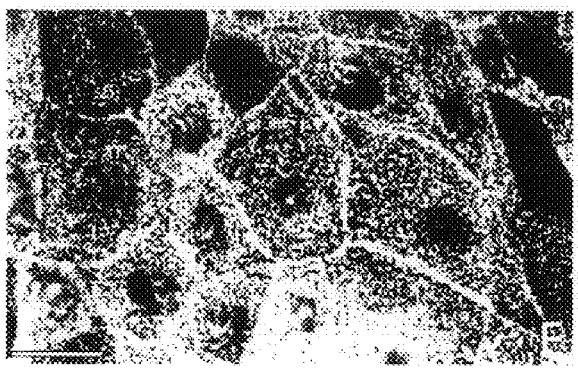
FIG. 2 shows the establishment of LLC-PK1 cell lines overexpressing wild type ezrin (E1, E2) or ezrin mutant tyr 353 to Phe (F1, F2).
Figure 2C:

FIG. 2 (panel a) shows an immunodetection performed with anti-tag antibody. Tagged ezrin is only detected in transfected cells.

FIG. 2 (panel b) shows an immunodetection performed with the anti ezrin antibody.

FIG. 2 (panel c) shows an immunolocalization of ezrin in LLC-PK1 cells overproducing wild-type ezrin (top panel) or ezrin mutant (bottom panel).

Figure 3A:
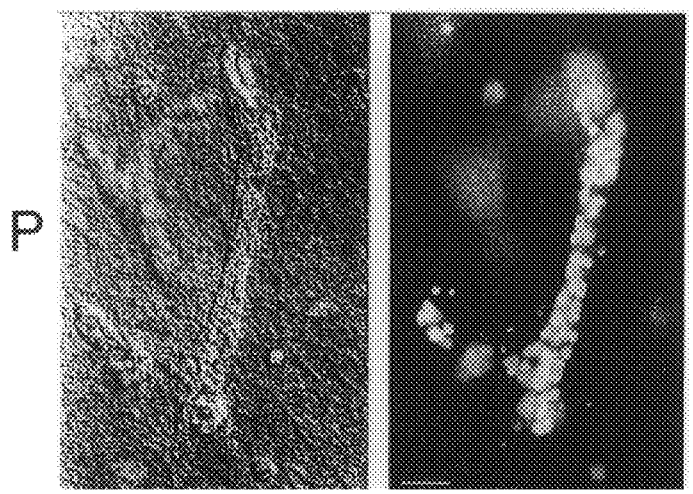
Figure 3B:
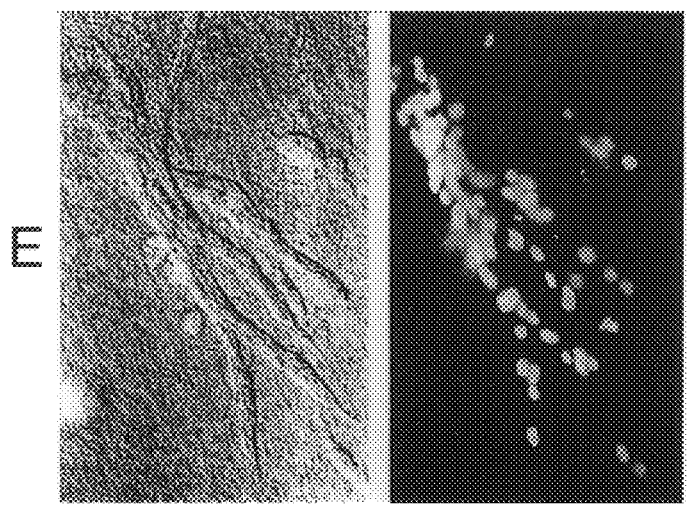
Figure 3C:
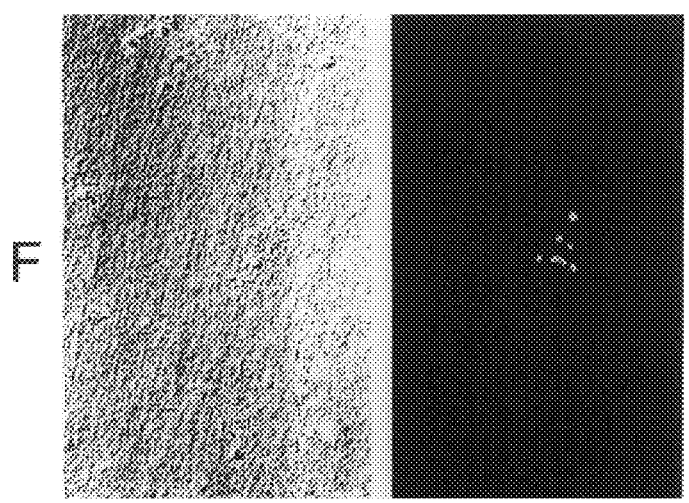

FIG. 3 shows three cell lines (E: cells overexpressing wild type ezrin; F: cells overexpressing ezrin mutant; P: cells transfected with the vector alone), grown in a collagen matrix in presence of HGF. F cells undergo apoptosis.

Figure 4A:
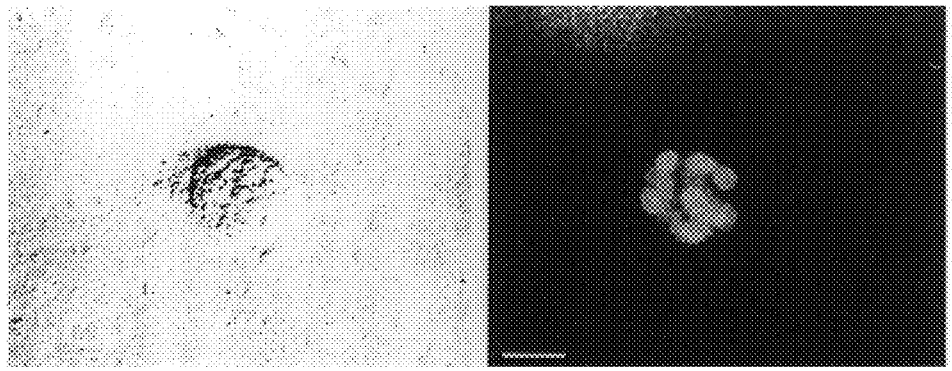
Figure 4B:
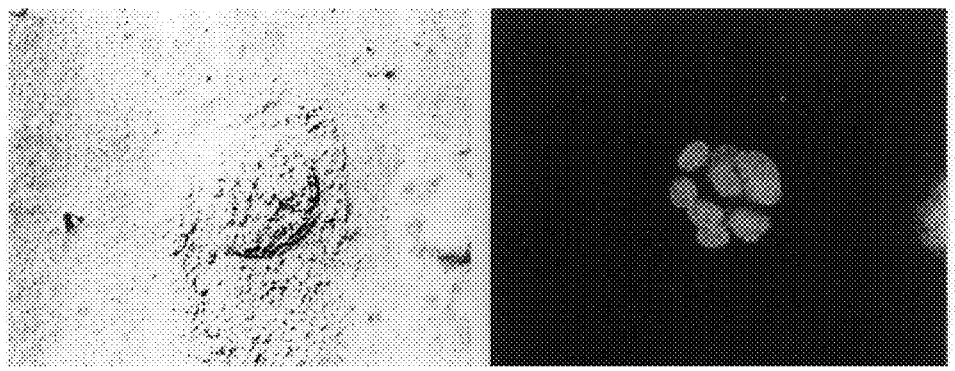
Figure 4C:
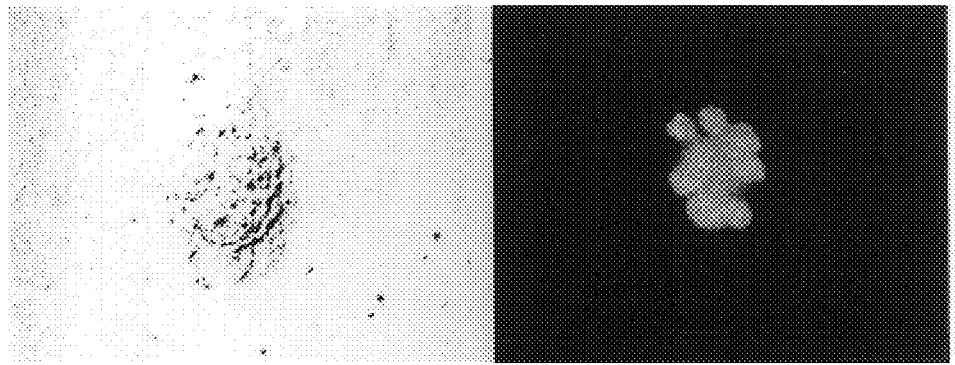

FIG. 4 shows three cell lines (E: cells overexpressing wild type ezrin; F: cells overexpressing ezrin mutant; P: cells transfected with the vector alone), grown in Matrigel®, gels. Cells do not form tubules. F calls do not undergo apoptosis.

Figure 5A:
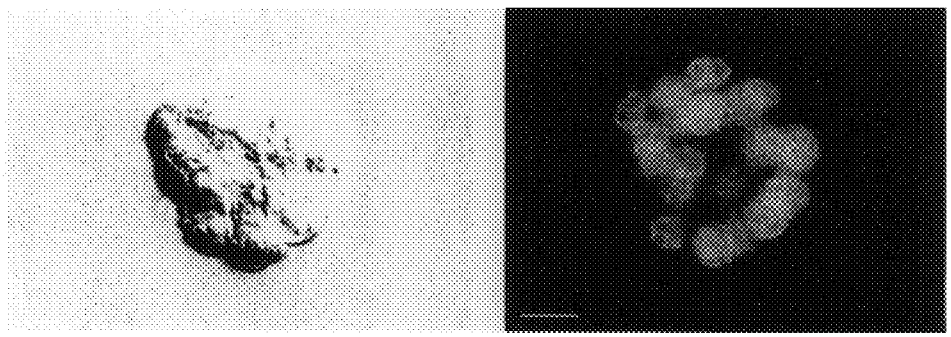
Figure 5B:
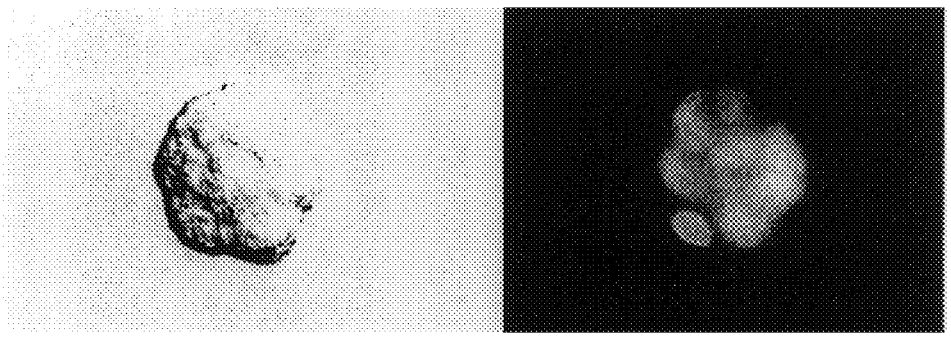
Figure 5C:
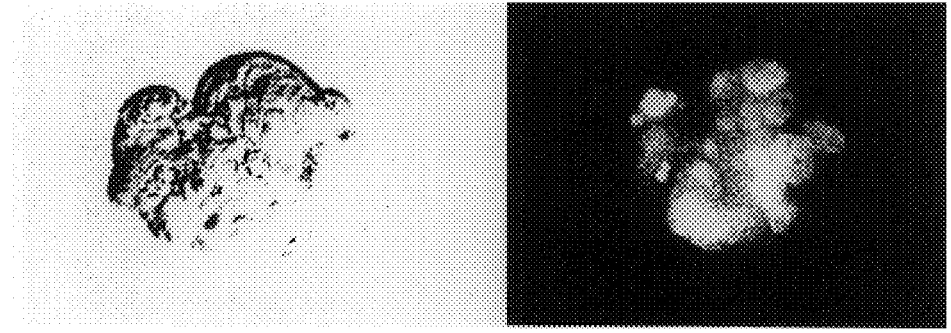

FIG. 5 shows three cell lines (E : cells overexpressing wild type ezrin; F: cells overexpressing ezrin mutant; P: cells transfected with the vector alone), grown in poly HEMA coated dishes. F cells undergo apoptosis. Piknotic nuclei are observed in cell aggregates.

Figure 6:
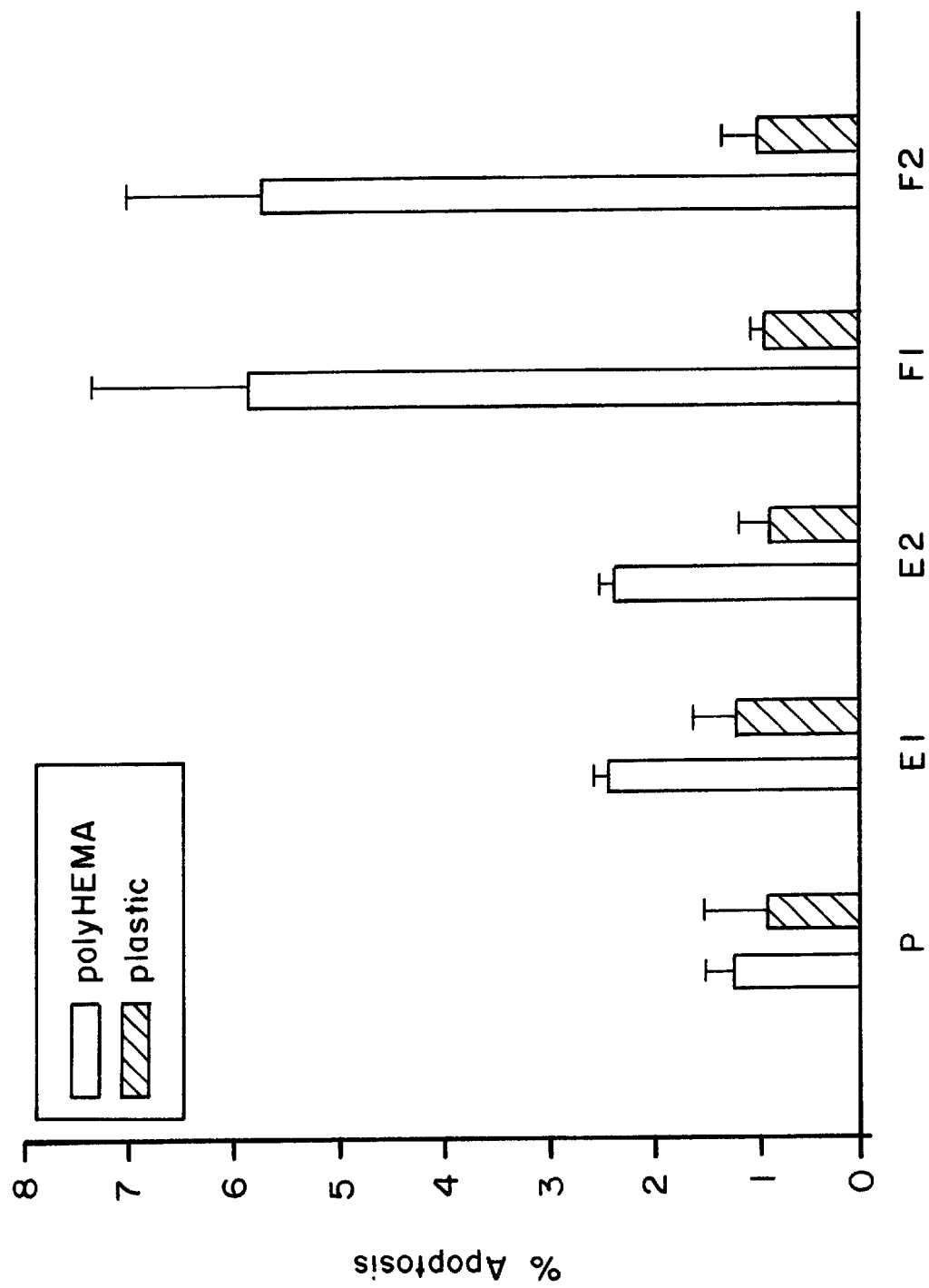

FIG. 6 shows an estimation of the percentage of apoptotic cells grown on poly HEMA compared to cells grown on plastic dishes.

Figure 7A:
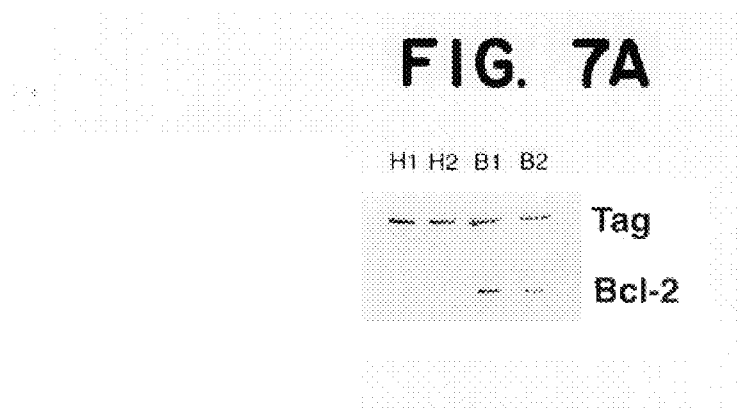
Figure 7B:
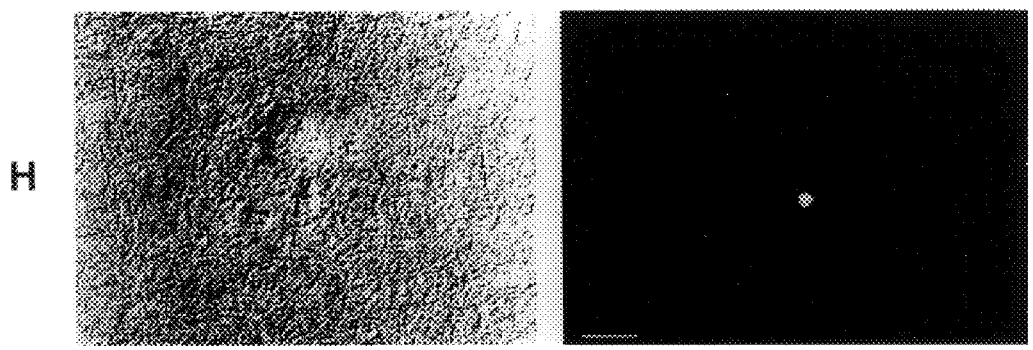
Figure 7C:
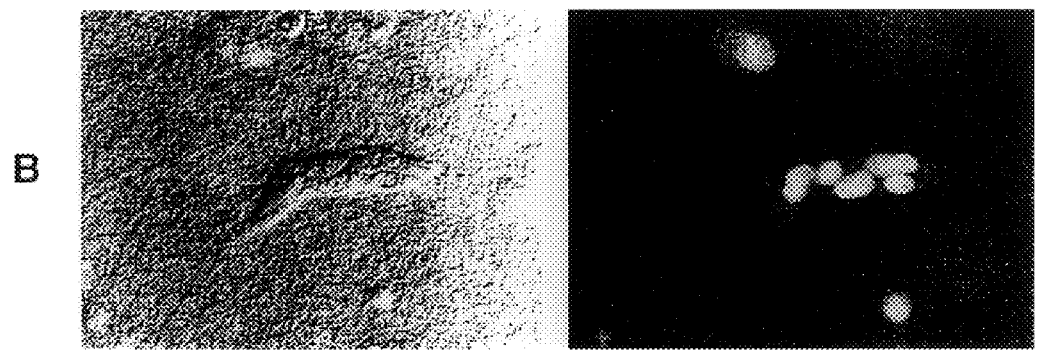

FIG. 7 shows DNA ladder showing apoptosis in F cells and also shows cells overexpressing Bcl-2 (B) and F353 cells transfected with the vector alone (H), grown in a collagen matrix. Bcl-2 can preserve the cells from apoptosis.

Figure 8:
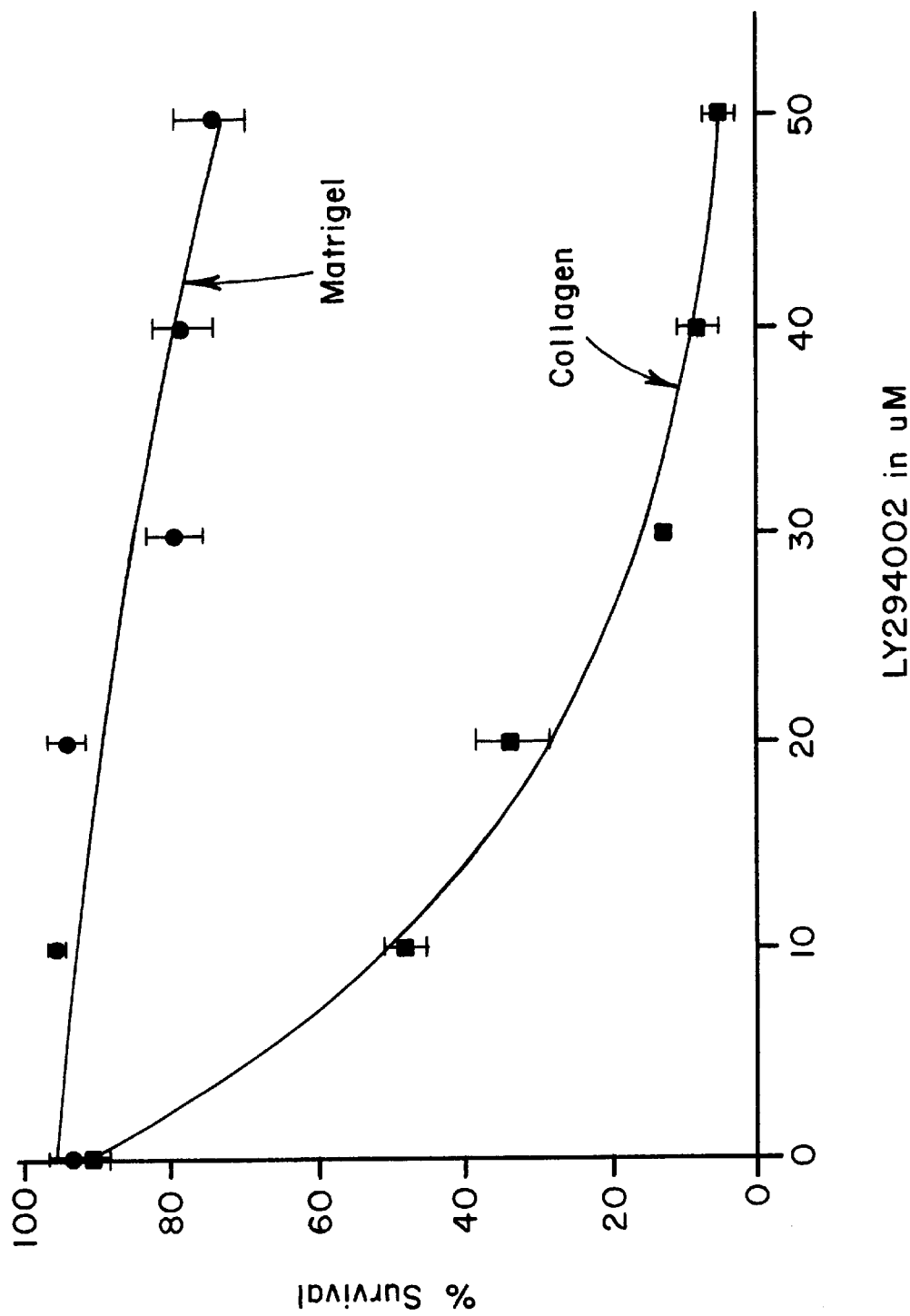

FIG. 8 is a graph showing LLC-PK1 cell survival in function of the concentration of the P13-K inhibitor, LY 294002.

Figures 6A, 9:
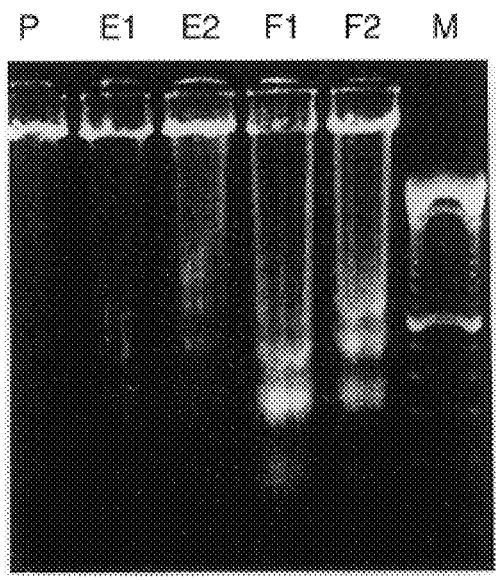

FIG. 9 shows an SDS-PAGE electrophoresis with the peptide: biotin-RQIKIWFQNRRMKWKKLRL QDYEEKTK(SEQ ID No: 2), or with the phosphorylated peptide: biotin-RQIKIWFQNRRMKWKKLRLQD(pY)EEKTK(SEQ ID No: 2). Lane 0 is blank. The P13-K-p85 subunit specifically interacts with the phosphorylated peptide.

MODES FOR CARRYING OUT THE INVENTION

Figure 1A:
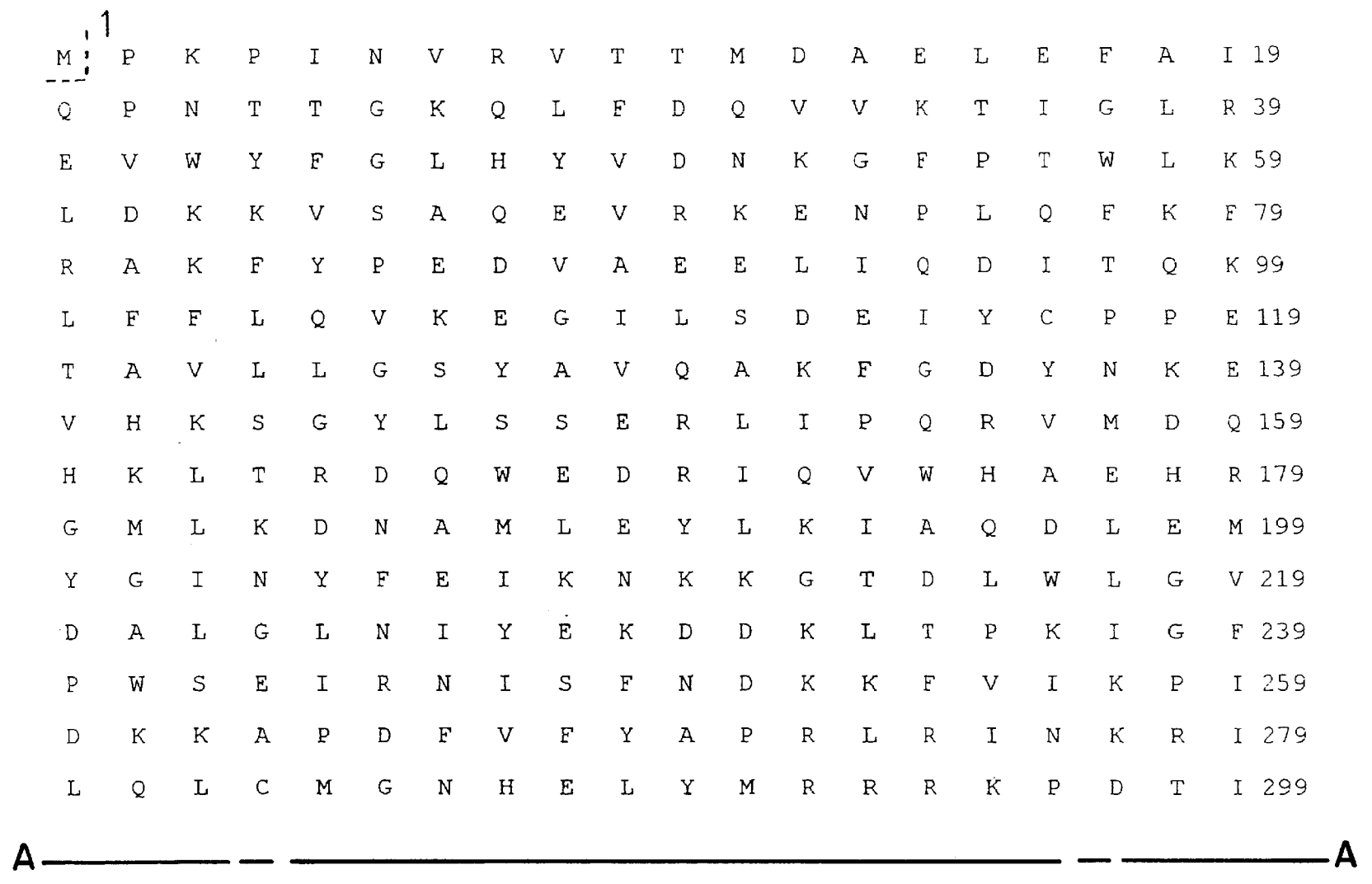

The amino acid sequence of native human ezrin is shown in FIG. 1. The expression "ezrin mutated on tyrosine 353" or "Y353 ezrin mutant" refers to a polypeptide having the sequence shown of FIG. 1, except for the amino acid 353 which is different from a tyrosine residue.

The amino acid 353 of the Y353 ezrin mutant may be preferably a phenylalaline residue, but may also be any other amino acid residue which cannot be phosphorylated.

Said Y353 ezrin mutant may be produced from native ezrin by site-directed mutagenesis, which is a technique well-known in the art (Crepaldi et al., 1997).

The term "functional derivative" is understood to refer to any polypeptide variant of Y353 mutant or any molecule resulting from a genetic and/or chemical modification of Y353 ezrin mutant, that is to say obtained by mutation, deletion, addition, substitution and/or chemical modification of a single or of a limited number of amino acids, as well as any isoform sequence, that is to say a sequence which is identical to the Y353 ezrin mutant sequence, except for one or more amino acids in the form of the D enantiomer, the said isoform, modified or variant sequences having conserved the biological activity of the Y353 ezrin mutant.

The biological activity of the Y353 ezrin mutant refers to the ability of Y353 ezrin mutant to induce apoptosis.

More particularly the biological activity of the Y353 ezrin mutant refers to the property of the Y353 ezrin mutant to impair the ability of cells to survive in a collagen matrix, more particularly in a matrix containing collagen type I or to grow in aggregates in suspension. This indicates that signaling from cell-cell and cell-substratum contacts is impaired.

The term "derivatives" thus comprises any polypeptide having an amino acid sequence which is substantially identical to the Y353 ezrin mutant in which one or more residues have been conservatively replaced by a functionally similar residue and which demonstrates its ability to mimic the Y353 ezrin mutant as described in the present invention. Examples of conservative replacements include the replacement of a hydrophobic residue such as isoleucine, valine, leucine or methionine with another hydrophobic residue, the replacement of a polar residue such as arginine with lysine, glutamine with asparagine or glycine with serine, the replacement of a basic residue such as lysine, arginine or histidine with another basic residue or the replacement of an acidic residue such as aspartic acid and glutamic acid with another acidic residue.

Similarly, the term "derivatives" comprises any polypeptide having one or more residues which are derived chemically from Y353 ezrin mutant by reaction of a functional group. Such derived molecules include, for example, molecules in which the free amino groups have been substituted in order to form amine hydrochlorides. The free carboxylic acid groups may be derived in order to form salts, methyl or ethyl esters or other types of esters or hydrazides. The free hydroxyl groups may be substituted in order to form O-acyl or O-alkyl derivatives. The imidazole nitrogen of the histidine may be substituted in order to form N-imidazole benzylhistidine. Peptides which contain one or more derivatives of an amino acid in its natural form from the 20 natural amino acids are also included as chemical derivatives. For example, proline may be replaced with 4-hydroxyproline; lysine may be replaced with 5-hydroxylysine; histidine may be replaced with 3-methyl-histidine; serin may be replaced with homoserine; and lysine may be replaced with ornithine.

The term "functional fragment" is understood to refer to any polypeptide having an amino acid sequence selected from any part of Y353 ezrin mutant sequence, and containing of course said amino acid 353. Preferred fragments contain at least the amino acid sequence between amino acid 350 and amino acid 356 as shown on FIG. 1.

According to one embodiment of the invention, naked polynucleotides are administered into a patient to achieve controlled expression of the Y353 ezrin mutant or fragments or derivatives thereof.

Said polynucleotides are DNA or RNA sequences encoding the Y353 ezrin mutant or encoding fragments or derivatives thereof, operatively linked to the genetic elements necessary for their expression by a target cell, such as promoters and the like.

The DNA or RNA encoding ezrin mutated on tyrosine 353, or encoding fragments or derivatives thereof, may be inserted into an expression vector, in which it is operatively linked to components which allow its expression to be regulated, in particular such as transcription promoters and/ or terminators.

Such an expression vector may be in particular a plasmid, a phage or any type of recombinant virus.

Among the prokaryotic transformation vectors which are well known to those skilled in the art, mention may be made of the ZAP Lambda phage vector and the pbluescript plasmid (Stratagene). Other vectors which are suitable for the transformation of E coli cells include pET expression vectors (Novagen) for example, pET11a, which contains the T7 promoter, the T7 terminator, the E. coli inducible Lac operon and the Lac repressor gene; and pET 12a–c, which contains the T7 promoter, the T7 terminator and the E. coli omPT secretion signal.

The vectors which are particularly preferred for the transfection of mammalian cells are vectors containing the cytomegalovirus (CMV) promoters such as pcDNA1 (Invitrogen), vectors containing the MMTV promoter such as pMAMNeo (Clontech) and pMSG (catalogue n° 27-4506-01 from Pharmacia) and vectors containing the SV40 promoter such as pSVβ (Clontech).

In the present invention, a promoter refers to a DNA segment which controls the transcription of DNA to which it is operatively linked. The promoter region includes specific sequences which are sufficient for recognition of the RNA polymerases, for binding and the initiation of transcription. In addition, the promoter region includes sequences which modulates this recognition, and the initiation of the binding and of the transcription of the RNA polymerase activity. As examples of promoters considered for use in the present invention, mention may be made of the SV40 promoter, the cytomegalovirus promoter, the mouse mammary tumour virus promoter (induced by steroids) and the Maloney murine leukemia virus promoter.

The pharmaceutical compositions of the invention may be administered to any animal which may experience the beneficial effects of the compositions of the invention. Foremost among such animals are humans, although the invention is not intended to be so limited.

DNA or RNA sequences encoding the Y353 ezrin mutant or encoding functional fragments or derivatives thereof can be administered to the patient by any method that delivers injectable materials to cells of the patient, such as by injection into the interstitial space of tissues such as muscles or skin, introduction into the circulation or into body cavities or by inhalation or insufflation. A naked polynucleotide is injected or otherwise delivered to the animal with a pharmaceutically acceptable liquid carrier. For all applications, the liquid carrier is aqueous or partly aqueous, comprising sterile, pyrogen-free water. The pH of the preparation is suitably adjusted and buffered.

The pharmaceutical compositions of the present invention (containing an effective amount of ezrin mutated on tyrosine 353, or a functional fragment or derivative thereof or containing an effective amount of DNA or RNA encoding ezrin mutated on tyrosine 353, or encoding functional fragments or derivatives thereof), may be administered by any means that achieve the intended purpose. For example, administration may be by parenteral, subcutaneous, intravenous, intradermal, intramuscular, intraperitoneal, or transdermal routes. Alternatively, or concurrently, administration may be by the oral route. The peptides and pharmaceutical compositions can be administered parenterally by bolus injection or by gradual perfusion over time.

Ezrin mutated on tyrosine 353, or a functional fragment or derivative thereof or DNA or RNA encoding ezrin mutated on tyrosine 353, or encoding functional fragments or derivatives thereof must be targeted toward tumor cells. For that purpose, the pharmaceutical compositions of the invention can be administered by direct injection to tumor aggregates.

Specific targeting to tumor cells may also be achieved by coupling Y353 ezrin mutant peptide with an antibody which specifically recognizes tumor cells. Y353 ezrin mutant peptide may also be delivered to tumor cells by liposomes carrying antibodies specific for tumor cells.

The dosage administered will be dependent upon the age, sex, health and weight of the recipient, kind of concurrent treatment, if any, frequency of treatment, and the nature of the effect desired.

The dose ranges for the administration of the composition of the present invention are those large enough to produce the desired effect. The doses should not be so large as to cause adverse side effects Preferred doses of the Y353 ezrin mutant peptide for humans range between about $10^{-9}$–$10^{-3}$ moles for one intratumoral injection. Injections are performed as necessary, the rate and amount being determined by the practioner.

In addition to the Y353 ezrin mutant and its derivatives which themselves are pharmacologically active, pharmaceutical compositions may contain suitable pharmaceutically acceptable carriers comprising excipients and auxiliaries which facilitate processing of the active compounds into preparations which can be used pharmaceutically. Preferred compositions include the inclusion of an adjuvant, such as alum, or other adjuvants known in the art.

To enhance delivery or bioactivity, the peptides (Y353 ezrin mutant and its derivatives) can be incorporated into liposomes using methods and compounds known in the art.

A further subject of the present invention is a method for the prevention and/or treatment of tumors, more particularly for the prevention and/or treatment of metastasis, comprising the administration to a patient in need of such treatment of an effective amount of a pharmaceutical composition according to the present invention.

All kinds of tumors are comprised. Tumors which are very likely to lead to metastasis are preferably aimed at. Examples of such tumors include epithelial cell tumors such as melanoma, and carcinoma.

The following examples and figures are intended to be illustrative but not to limit the invention.

EXAMPLES

Example 1

Construction of Ezrin Mutated on Tyrosine 353

Materials

LLC-PK1 (CCL 101; ATCC) cells were grown in DMEM growth medium (GIBCO BRL) supplemented with 10% fetal calf serum (FCS) and maintained at 37° C. in 10% $CO_2$.

Rabbit polyclonal anti-ezrin antibody was raised against the entire ezrin produced in bacteria and was previously described (Algrain et al., 1993).

DNA Constructs and Transfection

For generating the plasmid producing ezrin mutated on tyrosine 353 the following constructs were made. To make the F353 mutant (wherein Tyr353 is replaced by Phe353), the two oligonucleotides:

5' CGGAATTCCGGCTGCAGGACTTTGAGGAG 3' (SEQ ID No:3) and 5° CGCGGATCCATTGTGGGTC-CTCTTA 3' (SEQ No: 4) flanked with EcoRI and BamHI restriction sites respectively, were used to amplify the fragment (nucleotides 1125 to 1730) using the Ampli Taq polymerase (Perkin-Elmer Corp., Norwalk, Conn.). This fragment was then subcloned into the Bluescript plasmid and checked by double-strand DNA sequencing using the T7 sequencing kit (Pharmacia FineChemicals, Piscataway, N.J.). The fragment PstI-PstI corresponding to the sequence 1131 to 1197 and containing the mutated codon was inserted into the fragment AvaI-AvaI (nucleotides 1002–1698) in the plasmid psp64. The fragment AvaI-AvaI of the full length ezrin cDNA in the plasmid psp64 was then replaced by the fragment AvaI-AvaI containing the mutated codon. This mutant ezrin cDNA was then cloned in the expression vector pCB6 through the HindIII and XbaI restriction sites.

Exponentially growing LLC-PK1 cells were seeded 24 h before DNA transfer on 10-cm tissue culture dishes. DNA transfer was performed following the procedure of Chen and Okayama, (1987) and cells transfected were selected by growing in media containing 0.7 mg/ml Généticine (G-418), [Gibco BRL (Life Technologies) ref 11811-049] for 2–3 weeks.

For each transfection, three/four clones overproducing the transfected protein (as detected by immunoblot and immunofluorescence analysis) were selected for further study.

To generate the F353/bcl-2 cell lines, the F353 LLC-PK1 cells (clone 7) were transfected with 20 Tg of plasmid RSV-tk-hygromycin or plasmid RSV-tk-hygromycin-hbcl-2 by electroporation (240V and 950-TF) with the Gene Pulser II System (Bio-Rad, Hercules, Calif.). Transfected cells were selected with 0.2 mg/ml of hygromycin B in presence of 0.7 mg/ml G418. After 3 weeks of selection, individual colonies were isolated and expanded into cell lines.

Example 2

Establishment of LLC-PK1 Cell Lines

Overexpressing wild type Ezrin or Y353 Ezrin

Materials

P5D4 mAb raised against the 11-amino acid carboxy terminus of the vesicular stomatitis virus glycoprotein G (VSV-G peptide), was previously described (Kreis, 1986).

Results:
FIG. 2 shows the establishment of LLC-PK1 cell lines overexpressing wild type ezrin (E1, E2) or ezrin mutant tyr 353 to Phe (F1, F2).

The level of ezrin in cells overexpressing wild type ezrin (E) and ezrin mutant (F) was compared to the level of endogenous ezrin in cells transfected with the vector alone (P). Wild type and mutant ezrin were tagged with the VSV-G peptide at their carboxy-terminus. The immunodetection performed with anti ezrin antibody (FIG. 2B) shows that the level of transfected ezrin is 5–10 fold higher than the endogenous ezrin (lane P). The localization of ezrin mutant is similar to that of wild type ezrin in LLC-PK1 cells (FIG. 2C). There is not a striking morphological change when the cell lines are grown on plastic dishes.

Example 3

Biological Assays

Materials and Methods

For the tubulogenesis assay in three-dimensional collagen gels, the trypsinized cells were suspended at a final concentration of $1 \times 10^5$ cells/ml in gelling solution, prepared as follows: 1 part of DMEM 10×(GIBCO BRL), 1 part of $NaHCO_3$ (37 g/l), 1 part of FCS were mixed with 3.5 parts of a suspension of $3 \times 10^5$ cells/mil and 3.5 parts of type I collagen at 5 mg/ml (Collaborative Biomedical Products) at room temperature. 100 Tl of this mixture was seeded, in a microtiter plate, onto 100 Tl of a first layer of collagen without cell suspension. After 5 min at 37° C., the gels were covered with cell culture medium +/−. 100 U/ml HGF (the dia-filtered, human fibroblast MRC5-conditioned medium (Naldini et al., 1995), provided by Dr. C. Stella [Institute for Cancer Research (IRCC), University of Torino], was used as a source of Hepatocyte Growth Factor (HGF)). Photographs were taken with a light microscope (Leica) equipped with Nomarski interference optics. To assess apoptosis, the cells in the collagen preparation were fixed with methanol for 5 min and stained with HOECHST 33258 (10 Tg/ml). The preparations were examined with a Leica microscope equipped with a UV-absorbing filter. Condensed and fragmented nuclei were easily distinguishable from intact nuclei and percentage were calculated by counting.

Growth of LLC-PK1 cell lines was tested in a growth factor reduced Matrigel®, a soluble basal membrane extract which do not contain collagen type I (Becton Dickinson Labware, Bedford, Mass.). $1 \times 10^5$ cells (1 v) were mixed with Matrigel® (5 v) and gelation occurred at 37° C.

Results

1. The Survival of Ezrin Mutant is Impaired in a Collagen Matrix (FIG. 3)

When the three cell lines P, E, F were grown in a collagen matrix in presence of HGF striking differences between the three cell lines were observed. On the left panels, photographs were taken with a light microscope (Leica) equipped with Normarski interference optics. On the right panels, nuclei are labelled with the intercalating dye, Hoechst 33258. P and E cells developed tubules with more ramifications when cells overexpressed wild type ezrin (E). However no tubulogenesis is observed with F cells. The few cells observed present fragmented nuclei typical of apoptosis (F). This suggested that ezrin mutant impairs the ability of cells to survive in a collagen matrix.

2. Ezrin Mutant Survive in Matrigel® Gels (FIG. 4)

The ability of the three cell lines to grow in a Matrigel® gel was tested. All three cell lines were able to form cysts in the matrix and the F cell line did not undergo apoptosis as shown by analysis of the nuclei with the Hoechst dye (left panels). This indicated that ezrin is in the survival pathway elicited by collagen type I matrix and not by Matrigel®.

3. Cell Survival Mediated by Ezrin is Adhesion Dependent (FIGS. 5–6)

Growth of epithelial cells is anchorage dependent. When the three cell lines were grown on an anti-adhesive substrate, the poly HEMA coated dishes, P and E cells escape apoptosis through aggregation and formation of cysts (FIG. 5). In contrast, a significant proportion of F cells underwent apoptosis within aggregates. Apoptosis was estimated by two approaches. First DNA ladder (FIG. 6) shows that a higher level of DNA fragmentation occurred in F cells compared to P or E cells. Flow cytometric analysis allowed to estimate the percentage of apoptotic cells grown on poly HEMA compared to cells grown on plastic dishes. While the percentage of apoptotic cells is the same for all three clones grown on plastic dishes, the percentage of apoptotic cells is 2–3 times higher in F cells.

4. Bcl-2 Overexpression Rescues F353 Ezrin Mutants from Apoptosis (FIG. 7)

In order to confirm that apoptosis is due to a defect in signal transduction mediated by ezrin, cell lines overexpressing Bcl-2 from F353 cells have been established. The double transfected cell lines were tested for their ability to survive in a collagen matrix. FIG. 7 shows that cells overexpressing Bcl-2 survive in a collagen matrix (FIG. 7B) while F353 cells transfected with the vector alone do not (FIG. 7H). In addition, Bcl-2 transfected cells were able to form tubules, indicating that they did not lose their ability to interact with the collagen matrix.

Altogether these data indicate that ezrin is involved in a specific pathway mediating cell survival.

Furthermore, since P13-K (P13-kinase) has been shown to play a role in adhesion-dependent cell survival, it could be involved in this pathway.

Example 4

Treatment of LLC-PK1 Cells with the PI 3-Kinase Inhibitor, LY294002

Materials and methods

The effect of LY294002 (Sigma ref. L9908) was assessed on LLC-PK1 cells grown in type I collagen or Matrigele® matrices. $10^5$ cells/ml were embedded in the matrices and cultured, as previously described, in presence of 100 U/ml HGF. Cells were treated with LY294002 at increasing concentrations or with the vehicle DMSO. After 24 h, cultures were permeabilized with several changes of methanol 100% for 30 min at −20° C., and nuclei were stained with Hoechst 33258 (10 mg/ml in phosphate buffer saline). Condensed and intact nuclei were scored under microscope (Leica).

Results

FIG. 8 shows that LLC-PK1 cell survival is impaired by the P13-K inhibitor, LY294002.

LY294002 is a specific inhibitor of P13-K. When cells were grown in a collagen matrix in presence of various concentration of inhibitor, we observed a strong inhibition of cell survival at a concentration of LY294002 as low as 20 TM. No apoptosis is observed at the same concentration when the cells are grown in a Matrigel® matrix. This indicates that the cell survival signal elicited by the collagen matrix is P13-K and ezrin dependent.

Example 5 p85 Interaction with Phosphorylated Peptides

Materials and Methods

The authors of the present invention have designed peptides that contain a biotin fused to the Antennapedia internalization sequence (Derossi et al., 1994) in tandem with an eleven amino-acid peptide corresponding to the ezrin amino-acids 348–358. In one peptide, the tyrosine 353 was phosphorylated. The peptide sequence is: biotin-RQIKIWFQNRRMKWKKLRLQDY(p)EEKTK (SEQ No:2).

25 ml of Streptavidin Ultralink beads (Pierce, Rockford, Ill. USA) were pre-incubated with 300mg of biotinylated peptides for 1 h at 4° C. in buffer A (50 mM Hepes pH 7.4, 2 mM EDTA, 1% Triton X-100, 100 mM NaCl, 50 mM ammonium molybdate, 1 mM ZnC12). 7.106 LLC-PK1 cells grown on plastic dishes, were lysed with cold A buffer supplemented with a cocktail of protease inhibitors. Extracts were clarified by centrifugation, 10 min at 12000 g at 4° C. The beads were incubated with the extracts for 1 h, washed 3 times with buffer A, and re-suspended in SDS loading buffer. Samples were boiled and submitted to electrophoresis on SDS-PAGE.

Results

FIG. 9 shows that Ezrin phosphorylated peptide (aa 348–358) interacts with the P13-K p85 subunit.

The authors of the present invention made the hypothesis that interaction of the ezrin mutant with P13-K was altered. To test this hypothesis, an affinity column was performed with the ezrin peptides phosphorylated or not. As shown in FIG. 9 an interaction of P13-K p85 subunit is only observed with the phosphorylated peptide.

Altogether the above results indicate that:

Ezrin is involved in adhesion-dependent cell survival of epithelial cells.

Ezrin controls cell survival by activating the P13-K whose downstream target, in this pathway, is the serine/threonine kinase Akt.

This control is mediated by the interaction of the ezrin phosphorylated tyrosine residue 353 with the p85 subunit of the P13-K.

It is to be understood that while the invention has been described in conjunction with the above embodiments, that the foregoing description and the following examples are intended to illustrate and not limit the scope of the invention. For example, any of the above-noted compositions and/or methods can be combined with known therapies or compositions. Other aspects, advantages and modifications within the scope of the invention will be apparent to those skilled in the art to which the invention pertains.

REFERENCES

Algrain, M., O. Turunen, A. Vaheri, D. Louvard, and M. Arpin. 1993. Ezrin contains cytoskeleton and membrane binding domains accounting for its proposed role as a membrane-cytoskeletal linker. *J. Cell Biol.* 120:129–139.

Arpin et al. 1994. *Current Opinion in Cell Biology* 6:136–141.

Bardelli, A., F. Maina, I. Gout, M. J. Fry, M. D. Waterfield, P. M. Comoglio, and C. Ponzetto. 1992. Autophosphorylation promotes complex formation of recombinant hepatocyte growth factor receptor with cytoplasmic effectors containing SH2 domains. *Oncogene* 7:1973–1978.

Bretscher A. 1983. Purification of an 80 000 dalton protein that is a component of the isolated microvillus cytoskeleton and its localization in nonmuscle cells. *J. Cell. Bio*, 97, 425–432.

Chen, C., and H. Okayama. 1987. High-efficiency transformation of mammalian cells by plasmid DNA. *Mol Cell. Biol.* 7:2745–2752.

Crepaldi et al. 1997. *The Journal of Cell Biology* 138(2):423–434.

Derossi, D., A. H. Joliot, G. Chassaing, and A. Prochiantz. 1994. The third helix of the Antennapedia homeodomain translocates through biological membranes. *J. Biol Chem.* 269:10444–10450.

Kreig, J. and T. Hunter. 1992. Identification of the two major epidermal growth factor-induced tyrosine phosphorylation sites in the microvillar core protein ezrin, *J. Biol-Chem.* 267:19258–65.

Kreis, T. E. 1986. Microinjected antibodies against the cytoplasmic domain of vesicular stomatitis virus glycoprotein block its transport to the cell surface. *EMBO J.* 5:931–941.

Naldini, L., K. M. Weidner, E. Vigna, G. Gaudino, A. Bardelli, C. Ponzetto, R. P. Narsimhan, G. Hartmann, R. Zarnegar, and G. K. Michalopoulos. 1991. Scatter factor and hepatocyte growth factor are indistinguishable ligands for the MET receptor. *EMBO J.* 10:2867–2878.

Naldini, L., E. Vigna, A. Bardelli, A. Follenzi, P. Galimi, and P. M. Comoglio. 1995. Biological activation of pro-HGF (hepatocyte growth factor) by urokinase is controlled by a stoichiometric reaction. *J. Biol. Chem.* 270:603–611.

Tsukita et al.1997. *Current Opinion in Cell Biology* 9:70–75.

Vaheri et al. 1997. *Current Opinion in Cell Biology* 9:659–666.

What is claimed is:

1. An isolated polynucleotide encoding a polypeptide which exhibits an ability of an ezrin protein mutated on tyrosine 353 (Y353 ezrin mutant) to induce apoptosis, and has an amino acid sequence comprising an amino acid sequence of the Y353 ezrin mutant and further comprising at least seven contiguous amino acids of the Y353 ezrin mutant from residue 350 to residue 356 of SEQ ID NO:1.

2. The polynucleotide according to claim 1, wherein the polypeptide is an ezrin protein having the amino acid sequence set forth in SEQ ID NO:1, mutated on tyrosine 353.

3. The polynucleotide according to claim 1, wherein the polypeptide has the amino acid sequence set forth in SEQ ID NO:1 mutated on tyrosine 353 and wherein a hydrophobic amino acid flanking residues 350–356 of SEQ ID NO:1 is replaced by another hydrophobic amino acid.

4. The polynucleotide according to claim 1, wherein the polypeptide has the amino acid sequence set forth in SEQ ID NO:1 mutated on tyroslne 353 and wherein a polar amino acid flanking residues 350–356 of SEQ ID NO:1 is replaced by another polar amino acid.

5. The polynucleotide according to claim 1, wherein the polypeptide has the amino acid sequence set forth in SEQ ID NO:1 mutated on tyrosine 353 and wherein a basic amino acid flanking residues 350–356 of SEQ ID NO:1 is replaced by another basic amino acid.

6. The polynucleotide according to claim 1, wherein the polypeptide has the amino acid sequence set forth in SEQ ID NO:1 mutated on tyrosine 353 and wherein an acidic amino acid flanking residues 350–356 of SEQ ID NO:1 is replaced by another acidic amino acid.

7. The polynucleotide according to claim 1, wherein the polypeptide has the amino acid sequence set forth in SEQ ID NO:1 mutated on tyrosine 353 and wherein a praline residue flanking residues 350–356 of SEQ ID NO:1 is replaced by 4-hydroxyproline.

8. The polynucleotide according to claim 1, wherein the polypeptide has the amino acid sequence set forth in SEQ ID NO:1 mutated on tyrosine 353 and wherein an histidine residue flanking residues 350–356 of SEQ ID NO:1 is replaced by N-imidazole benzylhistidine.

9. The polynucleotide according to claim 1, wherein tyrosine 353 is mutated into a phenylalanine residue.

10. An isolated vector comprising the polynucleotide according to claim 1.

11. A host cell, comprising the vector according to claim 10.

12. A composition comprising the vector according to claim 10.

13. A method for inducing apoptosis in tumor cells, which method comprises directly administering to the tumor cells an effective amount of the composition according to claim 12, so as to induce apoptosis in the tumor cells.

14. The method according to claim 13, wherein the tumor cells comprise metastatic cells.

15. A method for inducing apoptosis in tumor cells, which method comprises directly administering to the Tumor cells an effective amount of the vector according to claim 10, so as to induce apoptosis in the tumor cells.

16. The method according to claim 15, wherein the tumor cells comprise metastatic cells.

* * * * *

UNITED STATES PATENT AND TRADEMARK OFFICE
CERTIFICATE OF CORRECTION

PATENT NO. : 6,399,584 B1
DATED : June 4, 2002
INVENTOR(S) : Monique Arpin et al.

It is certified that error appears in the above-identified patent and that said Letters Patent is hereby corrected as shown below:

<u>Title page,</u>
Item [75], Inventors: replace "Tiziana Crepaldi, Turin (IT);" with
-- Tiziana Crepaldi, Torino (IT) --

Item [73], Assignee: replace "Centre National de Recherche Scientfique, Paris (FR)" with -- Centre National de la Recherche Scientifique, Paris (FR) --

Signed and Sealed this

Fourth Day of February, 2003

JAMES E. ROGAN
*Director of the United States Patent and Trademark Office*

SEQUENCE LISTING

<160> NUMBER OF SEQ ID NOS: 4

<210> SEQ ID NO 1
<211> LENGTH: 586
<212> TYPE: PRT
<213> ORGANISM: Homo sapiens

<400> SEQUENCE: 1

Met Pro Lys Pro Ile Asn Val Arg Val Thr Thr Met Asp Ala Glu Leu
 1               5                  10                  15

```
Glu Phe Ala Ile Gln Pro Asn Thr Thr Gly Lys Gln Leu Phe Asp Gln
            20                  25                  30

Val Val Lys Thr Ile Gly Leu Arg Glu Val Trp Tyr Phe Gly Leu His
        35                  40                  45

Tyr Val Asp Asn Lys Gly Phe Pro Thr Trp Leu Lys Leu Asp Lys Lys
        50                  55                  60

Val Ser Ala Gln Glu Val Arg Lys Glu Asn Pro Leu Gln Phe Lys Phe
 65                  70                  75                  80

Arg Ala Lys Phe Tyr Pro Glu Asp Val Ala Glu Leu Ile Gln Asp
                85                  90                  95

Ile Thr Gln Lys Leu Phe Phe Leu Gln Val Lys Glu Gly Ile Leu Ser
                100                 105                 110

Asp Glu Ile Tyr Cys Pro Pro Glu Thr Ala Val Leu Leu Gly Ser Tyr
            115                 120                 125

Ala Val Gln Ala Lys Phe Gly Asp Tyr Asn Lys Glu Val His Lys Ser
        130                 135                 140

Gly Tyr Leu Ser Ser Glu Arg Leu Ile Pro Gln Arg Val Met Asp Gln
145                 150                 155                 160

His Lys Leu Thr Arg Asp Gln Trp Glu Asp Arg Ile Gln Val Trp His
                165                 170                 175

Ala Glu His Arg Gly Met Leu Lys Asp Asn Ala Met Leu Glu Tyr Leu
            180                 185                 190

Lys Ile Ala Gln Asp Leu Glu Met Tyr Gly Ile Asn Tyr Phe Glu Ile
        195                 200                 205

Lys Asn Lys Lys Gly Thr Asp Leu Trp Leu Gly Val Asp Ala Leu Gly
        210                 215                 220

Leu Asn Ile Tyr Glu Lys Asp Asp Lys Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
            260                 265                 270

Arg Leu Arg Ile Asn Lys Arg Ile Leu Gln Leu Cys Met Gly Asn His
        275                 280                 285

Glu Leu Tyr Met Arg Arg Arg Lys Pro Asp Thr Ile Glu Val Gln Gln
        290                 295                 300

Met Lys Ala Gln Ala Arg Glu Glu Lys His Gln Lys Gln Leu Glu Arg
305                 310                 315                 320

Gln Gln Leu Glu Thr Glu Lys Lys Arg Arg Glu Thr Val Glu Arg Glu
                325                 330                 335

Lys Glu Gln Met Met Arg Glu Lys Glu Glu Leu Met Leu Arg Leu Gln
            340                 345                 350

Asp Tyr Glu Glu Lys Thr Lys Lys Ala Glu Arg Glu Leu Ser Glu Gln
        355                 360                 365

Ile Gln Arg Ala Leu Gln Leu Glu Glu Glu Arg Lys Arg Ala Gln Glu
        370                 375                 380

Glu Ala Glu Arg Leu Glu Ala Asp Arg Met Ala Ala Leu Arg Ala Lys
385                 390                 395                 400

Glu Glu Leu Glu Arg Gln Ala Val Asp Gln Ile Lys Ser Gln Glu Gln
                405                 410                 415

Leu Ala Ala Glu Leu Ala Glu Tyr Thr Ala Lys Ile Ala Leu Leu Glu
            420                 425                 430

Glu Ala Arg Arg Arg Lys Glu Asp Glu Val Glu Glu Trp Gln His Arg
```

```
                   435            440           445
Ala Lys Glu Ala Gln Asp Asp Leu Val Lys T hr Lys Glu Glu Leu His
        450             455            460
Leu Val Met Thr Ala Pro Pro Pro Pro P ro Pro Val Tyr Glu Pro
465             470             475            480
Val Ser Tyr His Val Gln Glu Ser Leu Gln A sp Glu Gly Ala Glu Pro
                485             490            495
Thr Gly Tyr Ser Ala Glu Leu Ser Ser Glu G ly Ile Arg Asp Asp Arg
            500             505                510
Asn Glu Glu Lys Arg Ile Thr Glu Ala Glu L ys Asn Glu Arg Val Gln
        515             520            525
Arg Gln Leu Val Thr Leu Ser Ser Glu Leu S er Gln Ala Arg Asp Glu
    530             535            540
Asn Lys Arg Thr His Asn Asp Ile Ile His A sn Glu Asn Met Arg Gln
545             550             555            560
Gly Arg Asp Lys Tyr Lys Thr Leu Arg Gln I le Arg Gln Gly Asn Thr
                565             570            575
Lys Gln Arg Ile Asp Glu Phe Glu Ala Leu
            580             585

<210> SEQ ID NO 2
<211> LENGTH: 27
<212> TYPE: PRT
<213> ORGANISM: Homo sapiens
<220> FEATURE:
<221> NAME/KEY: variation
<222> LOCATION: (22)
<223> OTHER INFORMATION: Xaa = tyrosine or a phosphorylated tyrosine

<400> SEQUENCE: 2

Arg Gln Ile Lys Ile Trp Phe Gln Asn Arg A rg Met Lys Trp Lys Lys
  1               5              10                 15

Leu Arg Leu Gln Asp Xaa Glu Glu Lys Thr L ys
            20              25

<210> SEQ ID NO 3
<211> LENGTH: 29
<212> TYPE: DNA
<213> ORGANISM: Artificial Sequence
<220> FEATURE:
<223> OTHER INFORMATION: Description of Artificial  Sequence: primer
      (example 1)

<400> SEQUENCE: 3
cggaattccg gctgcaggac tttgaggag                                    29

<210> SEQ ID NO 4
<211> LENGTH: 25
<212> TYPE: DNA
<213> ORGANISM: Artificial Sequence
<220> FEATURE:
<223> OTHER INFORMATION: Description of Artificial  Sequence: primer
      (example 1)

<400> SEQUENCE: 4
cgcggatcca ttgtgggtcc tctta                                        25
```